US011162934B2

United States Patent
Scherer (10) Patent No.: US 11,162,934 B2
(45) Date of Patent: Nov. 2, 2021

(54) SMART BANDAGE (71) Applicant: California Institute of Technology, Pasadena, CA (US)

(72) Inventor: Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 789 days.

(21) Appl. No.: 15/913,704

(22) Filed: Mar. 6, 2018

(65) Prior Publication Data
US 2018/0267012 A1 Sep. 20, 2018

Related U.S. Application Data (60) Provisional application No. 62/471,493, filed on Mar. 15, 2017.

(51) Int. Cl.
G01N 33/483 (2006.01)
A61B 5/00 (2006.01)
(Continued)

(52) U.S. Cl.
CPC ....... *G01N 33/4836* (2013.01); *A61B 5/0531* (2013.01); *A61B 5/1486* (2013.01);
(Continued)

(58) Field of Classification Search
CPC .............. A61B 5/14546; A61B 5/1451; A61B 5/14532; A61B 5/6833; A61B 5/455; A61B 5/1486; A61B 5/145; A61B 5/14517; A61B 5/441; A61B 5/445; A61B 5/447; A61B 5/443; A61B 5/444; A61B 5/4836; A61B 2560/045; A61B 2562/164; A61B 5/6832;
(Continued)

(56) References Cited

U.S. PATENT DOCUMENTS 5,409,591 A * 4/1995 Baker ................ G01N 27/4074
204/412
5,578,022 A * 11/1996 Scherson .......... A61F 13/00068
604/304
(Continued)

FOREIGN PATENT DOCUMENTS

CN   104374765 A    2/2015
KR   20140001612   1/2014
(Continued)

OTHER PUBLICATIONS

MacKay, Scott; Wishart, David; Xing, James Z.; Chen, Jie, "Developing Trends in Aptamer-Based Biosensor Devices and Their Applications," Feb. 2014, IEEE Transactions on Biomedical Circuits and Systems, vol. 8, No. 1, p. 4-14 (Year: 2014).*
(Continued)

*Primary Examiner* — Eric F Winakur
*Assistant Examiner* — Alice Ling Zou
(74) *Attorney, Agent, or Firm* — Steinfl + Bruno LLP (57) ABSTRACT

A sensing chip attached to a bandage monitors the healing process of a wound by detecting growth factors, thrombin and fibrinogen. The complementary metal-oxide semiconductor includes a functionalized working electrode, functionalized counter electrode and functionalized reference electrode. The healing progress is stimulated by generating oxygen in the wound.

10 Claims, 7 Drawing Sheets (51) Int. Cl.

| | |
|---|---|
| *G01N 27/414* | (2006.01) |
| *A61F 13/00* | (2006.01) |
| *A61B 5/0531* | (2021.01) |
| *A61B 5/145* | (2006.01) |
| *A61B 5/1473* | (2006.01) |
| *A61B 5/1486* | (2006.01) |

(52) U.S. Cl.
CPC .......... *A61B 5/14546* (2013.01); *A61B 5/445* (2013.01); *A61B 5/4848* (2013.01); *A61B 5/6833* (2013.01); *A61F 13/00051* (2013.01); *G01N 27/4148* (2013.01); *A61F 2013/00314* (2013.01)

(58) Field of Classification Search
CPC ... A61B 5/6802; A61B 5/6801; A61B 5/1477; A61P 9/10; A61P 17/02; A61K 9/0014; A61L 2430/34; A61L 2430/00; A61M 2202/0007; A61M 2202/0057; A61M 2202/0208; A61M 35/30; A61M 35/10; A61M 1/0088; A61M 2205/3592; A61M 2205/3584; A61M 2205/3553; A61M 2005/006
See application file for complete search history.

(56) References Cited

U.S. PATENT DOCUMENTS

| | | | | |
|---|---|---|---|---|
| 6,170,318 | B1* | 1/2001 | Lewis ................. | G01N 27/126 340/632 |
| 2006/0224072 | A1* | 10/2006 | Shennib .............. | A61B 5/6833 600/509 |
| 2009/0112295 | A1 | 4/2009 | Hyde et al. | |
| 2010/0252452 | A1 | 10/2010 | Newman et al. | |
| 2012/0209090 | A1* | 8/2012 | Goodall ............. | A61B 5/14503 600/309 |
| 2013/0274630 | A1* | 10/2013 | Duesterhoft ........ | A61B 5/1477 600/573 |
| 2014/0318958 | A1* | 10/2014 | Hassibi .............. | G01N 27/3277 204/403.01 |
| 2014/0375465 | A1 | 12/2014 | Fenuccio et al. | |
| 2015/0087935 | A1* | 3/2015 | Davis .................... | A61B 5/445 600/309 |
| 2015/0177180 | A1* | 6/2015 | Davis .................. | G01N 27/026 205/780.5 |
| 2016/0109401 | A1* | 4/2016 | Wardell ............. | G01N 33/5438 205/777.5 |

FOREIGN PATENT DOCUMENTS

| | | | |
|---|---|---|---|
| KR | 20160143977 A | 12/2016 | |
| WO | WO-2017173462 A1 * | 10/2017 | ............ A61B 5/053 |

OTHER PUBLICATIONS

Chue, Colin; Leo, Chemmanda John; Chan, Wai Pan; Damal. "Characterization of CMOS Electrochemical Oxygen Sensor for Biomedical Applications," 2015, IEEE International Conference on Electron Devices and Solid-State Circuits (EDSSC), p. 325-328 (Year: 2015).*

Eming, Sabine A; Koch, Manuel; Krieger, Andreas; Brachvogel, Bent; Kreft, Sandra; Bruckner-Tuderman, Leena; Krieg, Thomas; Shannon, John; Fox, Jay W, "Differential Proteomic Analysis Distinguishes Tissue Repair Biomarker Signatures in Wound Exudates Obtained from Normal Healing and Chronic Wounds," (Year: 2010).*

[Item W continued] Journal of Proteome Research, vol. 9, No. 9 , p. 4761-4764 (Year: 2010).*

Written Opinion and International Search Report for International application No. PCT/US2018/021216 filed Mar. 6, 2018 on behalf of California Institute of Technology, dated Jun. 25, 2018. 14 pages.

Deng, C., et al., "Impedimetric Aptasensor with Femtomolar Sensitivity Based on the Enlargement of Surface-Charged Gold Nanoparticles," *Analytical Chemistry*, vol. 81, No. 2, Jan. 15, 2009. pp. 739-745. 7 Pages. https://doi.org/10.1021/ac800958a.

Inoue, S., et al., "Multi-layered Aptamer Array Integrated in Microfluidic Chip for On-site Blood Analysis," *15th International Conference on Miniaturized Systems for Chemistry and Life Sciences* held on Oct. 2-6, 2011, Seattle, Washington, USA. pp. 1876-1878. 3 Pages.

Liu, S., et al., "Single-Molecule Detection of Proteins Using Aptamer-Functionalized Molecular Electronic Devices," *Angewandte Chemie International Edition*, vol. 50, Issue 11, Feb. 21, 2011. pp. 2496-2502. 7 Pages. https://doi.org/10.1002/anie.201006469.

Sook Bang, G., et al., "A novel electrochemical detection method for aptamer biosensors," *Biosensors and Bioelectronics*, vol. 21, Issue 6, Available online Mar. 25, 2005, pp. 863-870. 8 Pages. https://doi.org/10.1016/j.bios.2005.02.002.

Wang, W., et al., "Aptamer biosensor for protein detection based on guanine-quenching," *Sensors and Actuators*, vol. 129, Issue 1, Available online Aug. 6, 2007. pp. 211-217. 7 Pages. https://doi.org/10.1016/j.snb.2007.07.125.

Xu, D., et al., "Label-Free Electrochemical Detection for Aptamer-Based Array Electrodes," *Analytical Chemistry*, vol. 77, Issue 16, Aug. 15, 2005. pp. 5107-5113. 7 Pages. https://doi.org/10.1021/ac050192m.

* cited by examiner

SMART BANDAGE

CROSS REFERENCE TO RELATED APPLICATIONS

The present application claims priority to U.S. Provisional Patent Application No. 62/471,493, filed on Mar. 15, 2017, the disclosure of which is incorporated herein by reference in its entirety.

TECHNICAL FIELD

The present disclosure relates to monitoring wounds and accelerating wound healing. More particularly, it relates to a smart bandage for monitoring of wounds.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, a device is described, the device comprising: a bandage having a first surface configured to face a wound; a sensor attached to the bandage on the first surface.

In a second aspect of the disclosure, a method is described, the method comprising: providing a complementary metal-oxide semiconductor sensor chip comprising a working electrode, a counter electrode, and a reference electrode, the working electrode, the counter electrode, and the reference each having a gold surface; attaching the complementary metal-oxide semiconductor sensor chip to a bandage; attaching a thiol group to a thrombin binding aptamer; and attaching the thrombin binding aptamer with the thiol group to the gold surface of the working electrode, or of the counter electrode, or of the reference electrode.

DETAILED DESCRIPTION

The present disclosure describes a "smart bandage" for monitoring wounds and accelerating wound healing. Smart bandages can be fabricated by using inexpensive complementary metal-oxide semiconductor (CMOS) chips, placed into conventional bandages. For example, the chips can be powered wirelessly, or in any case capable of wireless communication. The chips, when attached to a bandage, are exposed to the complex chemistry of the wound. The chip can, for example, detect chemical or biological parameters in the wound. The sensor chips can, therefore, detect data which can indicate how a wound is healing or progressive. The data, communicated to a reader device, for example connected wirelessly to the chip, can then inform subsequent medical treatments. The medical treatments can therefore be more effective as they are based on detailed information of the state of the wound.

The possibility to create inexpensive, disposable smart bandages relies on the ability to produce and functionalize millimeter-scale CMOS chips, for example with a cost of approximately 10 cents/chip, using volume-based fabrication methods. This in turn can make smart bandages viable for a large market.

The process of wound healing can be summarized by the following sequence of events. When the skin is cut or scraped, bleeding starts. Blood cells begin to clump together and clot, instructed by proteins such as thrombin and fibrinogen. These protect the wound and prevent further blood loss (hemostasis). The clots, which turn into scabs and dry, are created by platelets, and contain fibrin, which forms a net to hold the clots in place.

Once the wound is closed with a clot, the blood vessels can open a bit to allow fresh nutrients and oxygen into the wound for healing. Oxygen is essential for healing, and the right balance of oxygen is very important. Too much or too little oxygen will prevent the wound from healing correctly. Macrophages (white blood cells) are used to fight infection and clear fluid is often expelled around the cut at that time. Macrophages also release growth factors that help repair the wound. This process is followed by strengthening of the repaired tissue, which is a process that can take several months.

The two important initial wound healing processes of hemostasis and inflammation are normally taken for granted and are not monitored very carefully. These typically take several days. Unfortunately, a wound that is not receiving enough blood could take at least twice as long to heal, if it heals at all. It is estimated that 6.5 million people in the United States suffer with wounds that are not healing well. Difficulties in wound healing often occur in populations that suffer from chronic wounds, typical in populations with diabetes, high blood pressure, obesity and other vascular disease.

Figure 1:
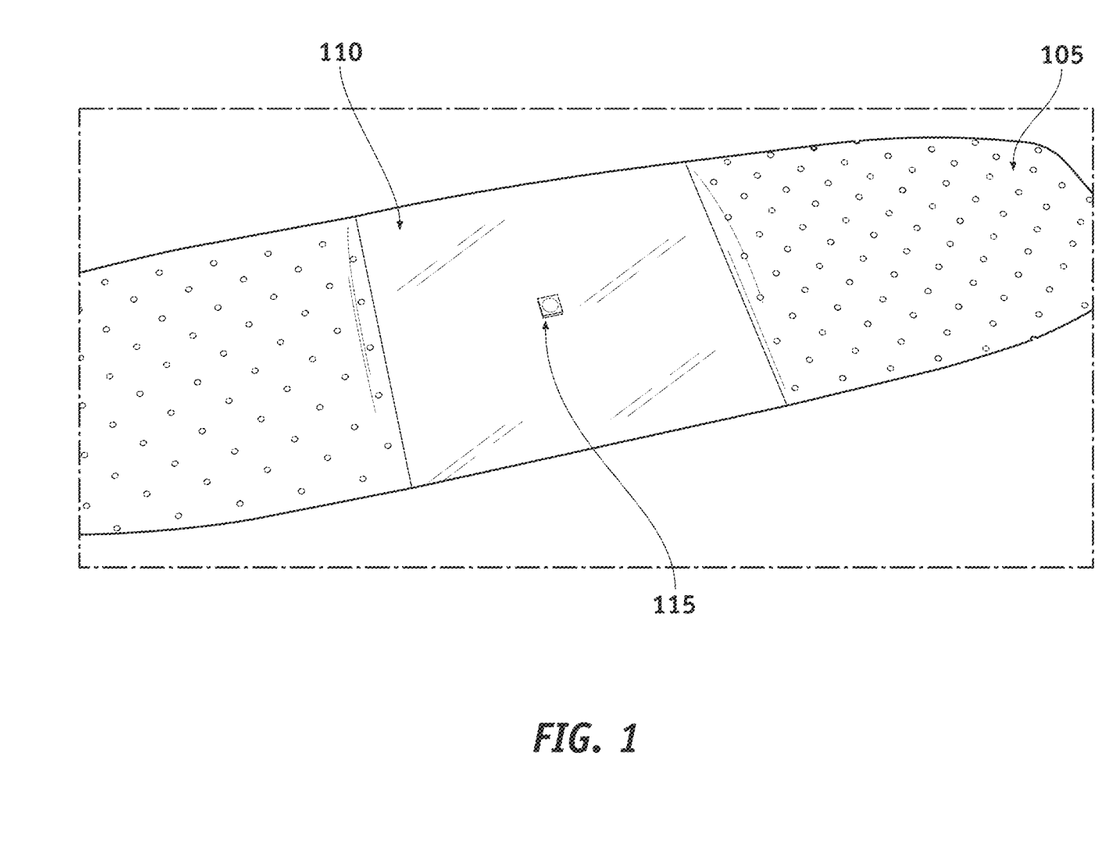
FIG. 1 illustrates an exemplary smart bandage.

The present disclosure describes the concept of inexpensive CMOS chips integrated in bandages or similar items. For example, FIG. 1 illustrates a band-aid or adhesive bandage, a common household item, which comprises an adhesive part (105), a gauze part (110), and a sensor chip (115). The sensor chip could also be integrated in gauze which is not part of an adhesive bandage or band-aid, but part of a strip of cloth or similar material that can be applied to a wound, for example by wrapping it around an arm or torso.

The chip attached to the bandage can monitor the process of hemostasis and inflammation, as well as identify infections in wounds. In some embodiments, the chips can also be modified to generate and measure oxygen locally in their surroundings, and carry chemistries that can be released on command. A reader device can be used to power and communicate with these chips, for example through a near-field inductive coil "antenna".

Currently, wound healing is generally monitored by visual observation. The personal experience of the health practitioner monitoring the wound is used to determine the progression of the healing process. Occasionally, molecular diagnostic tools need to be used to evaluate the chemistry of this process. Given the low anticipated cost of the diagnostic systems described in the present disclosure, as well as the large opportunities for adapting diagnostic chips for different types of injuries, wound healing chips will be very competitive as a value addition to the bandage market, which has experienced a lack of innovation over the past decades.

Figure 3:
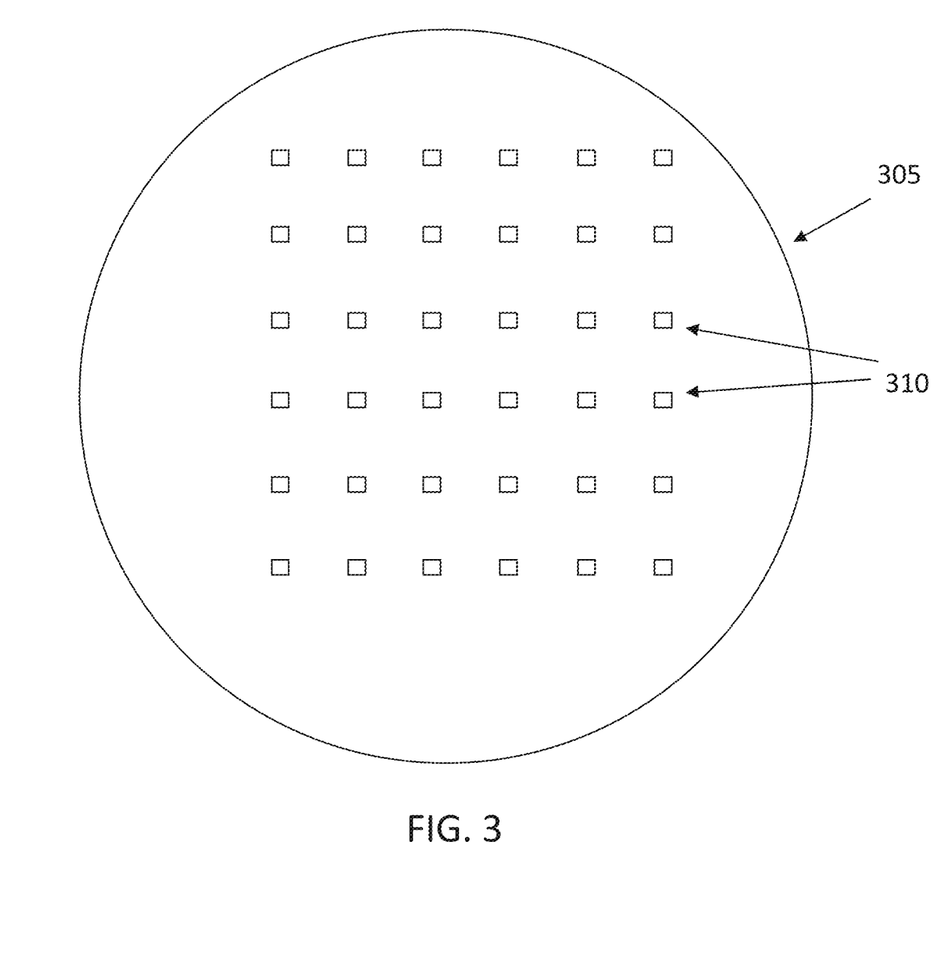
FIG. 3 illustrates an exemplary wafer with sensor chips.

One of the key advantages of using CMOS electronic chips as the basis for medical diagnostic measurements is the ability to leverage technical knowledge in the consumer electronics industry, into the fabrication of small but complex medical devices. In some embodiments, the smart bandage can comprise a wireless platform. The smart bandage can comprise a potentiostat chip to measure glucose in diabetes patients, containing, for example, 10,000 transistors and a wireless RF tag circuit link operating at 800-900 MHz to power and communicate with the reader device. For medical applications, the contact surfaces, typically aluminum-silicon alloys, can be to coated with platinum. Additionally, enzymes can be applied to these contact surfaces to functionalize the chips for the measurement of specific analytes (such as lactate, pyruvate, glucose, etc). This post-processing adds a fixed cost per device, but can be automated and performed at the wafer scale. FIG. 3 illustrates how multiple chips (310) can be fabricated on a single wafer (305) to decrease costs.

To read the sensor chips, a standard radiofrequency (RF) tag reader can be used. These tag readers have been developed for identification and tracking of materials and are commercially available. For example, an RF tag reader can be used for continuous glucose monitoring by connecting to the chip in the bandage and communicate with the chip continuously.

In some embodiments, it is possible to measure glucose by using the conversion of glucose into gluconic acid and hydrogen peroxide with the assistance of an enzyme—glucose oxidase or glucose dehydrogenase. For example, a standard set up comprising a working electrode, a counter electrode, and a reference electrode can be used. The current on the working electrode measures the hydrogen peroxide ion current resulting from the glucose reaction, and this current is proportional to the glucose concentration if the chemistry is well-controlled (i.e., enough oxygen is supplied to enable this reaction).

Figure 2:
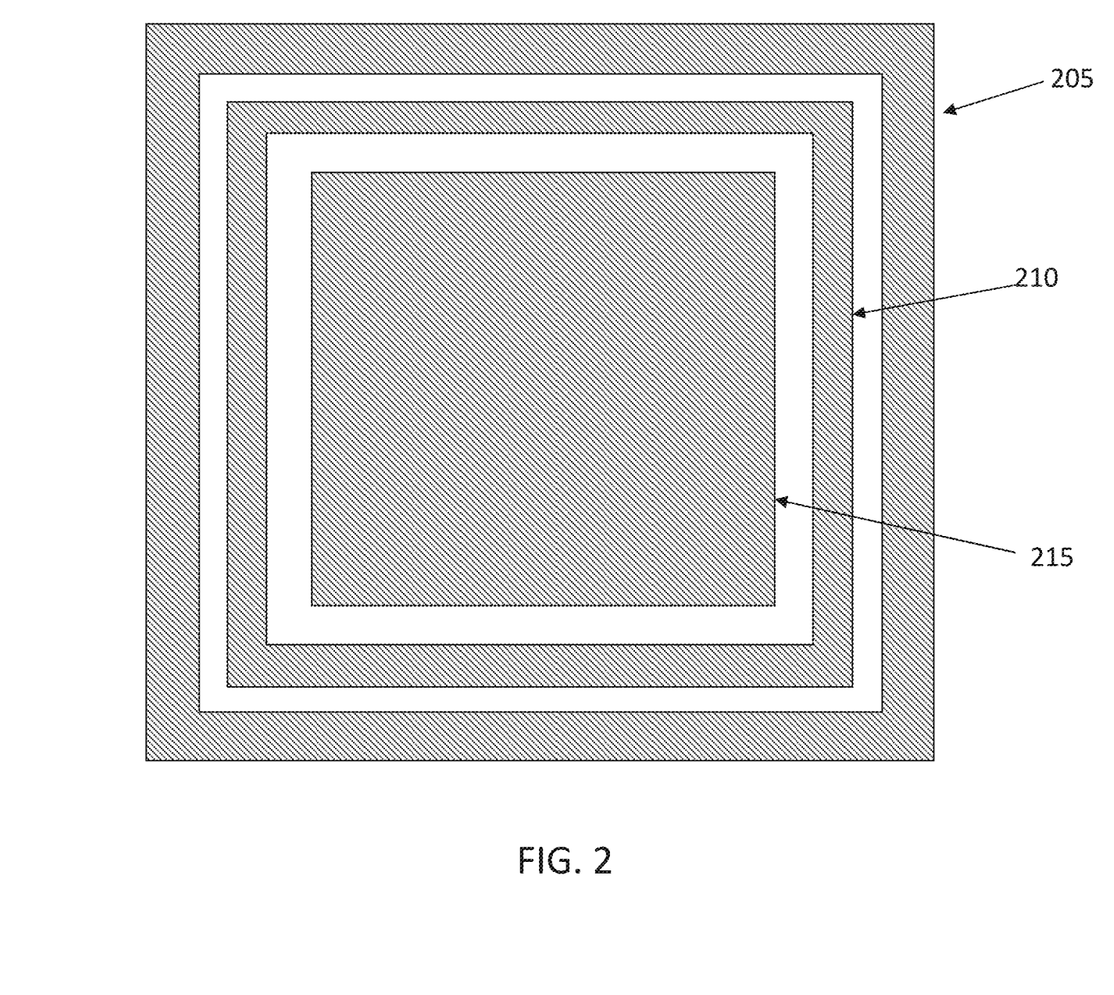
FIG. 2 illustrates an exemplary electrode setup for a sensor.

FIG. 2 illustrates an exemplary set of electrodes which can be fabricated on a surface of the chip, to face towards the wound when applying the smart bandage. For example, a working electrode (215), a counter electrode (205) and a reference electrode (210) can be fabricated as concentric squares, or other similar shapes. These electrodes can be functionalized to detect different biological entities in a wound, such as thrombin, fibrinogen, and growth factors, or others. For example, biological agents can be attached to the metallic surface as functionalization.

In other embodiments, the chips of the present disclosure can use the same powering and communications platform as the glucose monitoring chips, but can be able to measure thrombin, fibrinogen, and growth factors by using aptamer binding chemistry combined with conductivity measurements. Electrochemical oxygenation measurements can also be possible, along with the deliberate generation of oxygen through electrochemical dissociation of water. Physiological data, such as local chip temperature, can also be included into the sensor to enable the observation of the inflammation process. The combination of these measurements is able to provide an indication of the healing process, as well as an opportunity for early detection of infection.

Figure 4:
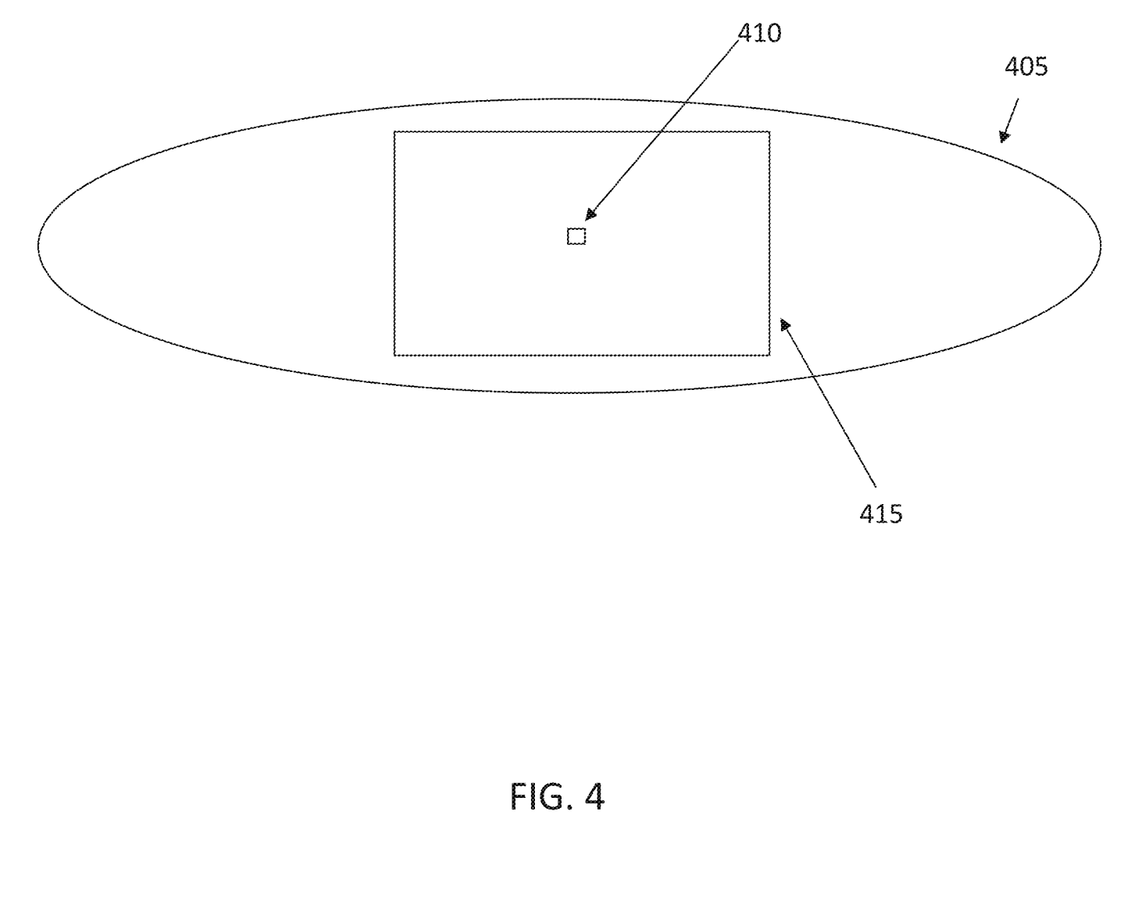
FIG. 4 illustrates an exemplary smart bandage.

FIG. 4 illustrates an exemplary adhesive bandage comprising an adhesive part (405), a gauze part (415), and a chip (410).

As known to the person of ordinary skill in the art, thrombin is a serine protease, an enzyme that cleaves peptide bonds in a protein. Fibrinogen is a glycoprotein that circulates in the blood. In a tissue or vascular injury, fibrinogen is converted enzymatically by thrombin to fibrin and subsequently to a fibrin-based blood clot. Fibrinogen functions primarily to occlude blood vessels and thereby stop excessive bleeding. Aptamers are oligonucleotide or peptide molecules that bind to a specific target molecule. Aptamers can be created by selecting them from a large random sequence pool. Nucleic acid aptamers are nucleic acid species that have been engineered through repeated rounds of selection or evolution to bind to molecular targets such as small molecules, proteins, nucleic acids, cells, or tissues. Peptide aptamers are artificial proteins selected or engineered to bind specific target molecules. Therefore, aptamers can be used to bind selectively to a desired biomolecular target, for example thrombin or fibrinogen. In this way, aptamers can be used to detect the presence and quantity of thrombin or fibrinogen. In some embodiments, the thrombin binding aptamer is attached to the surface of the electrodes in the sensing chip in the smart bandage. Upon binding to thrombin, the aptamer can become dissociated from the electrode surface, thus originating an electrical signal at the chip. For example, the impedance would change due to the surface change at the electrodes subsequent to target binding. Voltammetry measurements with a working electrode, counter electrode and reference electrode could be used. Generally, amperometric, voltammetric, or impedimetric signals for detection of thrombin or other biomolecular markers of wound healing can be used by the chip to monitor the evolution of the state of the wound.

For example, the thrombin binding aptamer can be attached to a gold electrode surface. The displacement event of the binding aptamer is based on the propensity of single-stranded DNA to readily absorb onto a gold surface, and to subsequently desorb upon binding to the aptamer's target, for example thrombin. A thiol functional group can be added to the binding aptamer for covalent binding to the gold surface. Other aptamers can be used to detect other biomolecular targets instead of thrombin.

For example, aptamers for human thrombin detection can be based on two non-overlapping DNA thrombin aptamers. As another example, thrombin binding to an immobilized thrombin binding aptamer on the surface of the chip can enable the chip to detect thrombin. For example, the aptamers can be attached to the surface of the electrodes to detect thrombin. Upon attachment, the electrical characteristic of the electrode would change, enabling the chip to detect the change in current or voltage.

The functionalized chips can be tested in-vitro to ensure that the aptamer chemistry is stable, contacts can be kept clean and active, and the sensors can provide quantitative information on the hemostatis and inflammation chemistries for several days. As the smart bandages do not involve a permanent implant, but will be disposed with the bandage after the wound is healed, it is expected that a lengthy FDA approval process can be avoided. Initial toxicology tests on the CMOS chips have revealed no change in the surrounding chemistry even after 3 months of exposure to tissue.

Currently, wound healing is performed using very empirical approaches. After cleaning of the wound and the application of a bandage, the wound is occasionally monitored, and infection is avoided. The collection of quantitative data with the smart bandages of the present disclosure allows development of an analytical molecular diagnostic tool to measure the healing progression and provide immediate feedback information to both patient and practitioner.

Wound care is predicted to grow modestly over the forecast period, with value sales increasing by 8% in constant 2013 terms to reach US $892 million in 2018. Gashes and cuts are a part of everyday life, and while enough people maintain an active lifestyle, they will continue to buy bandages at about the same rate as they have before.

Figure 5:
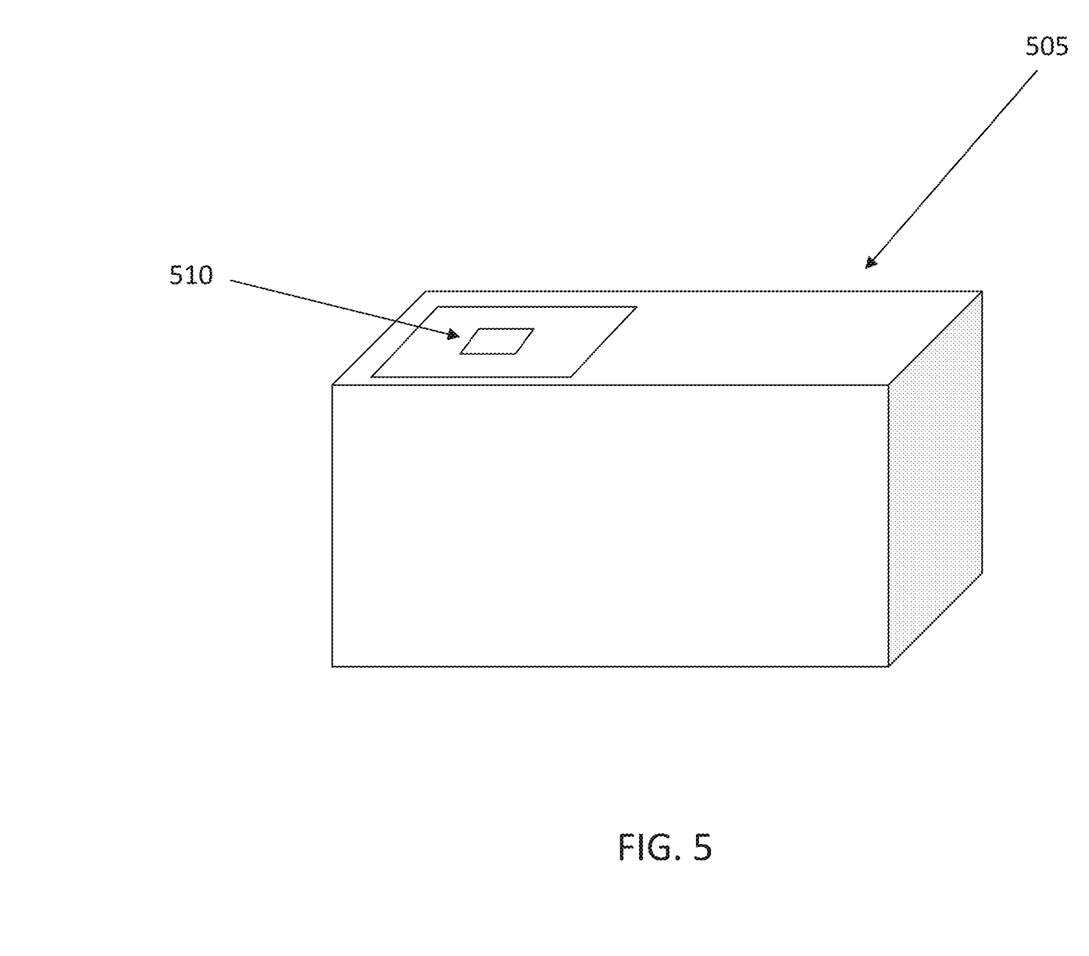
FIGS. 5-6 illustrate an exemplary reading device.
Figure 6:
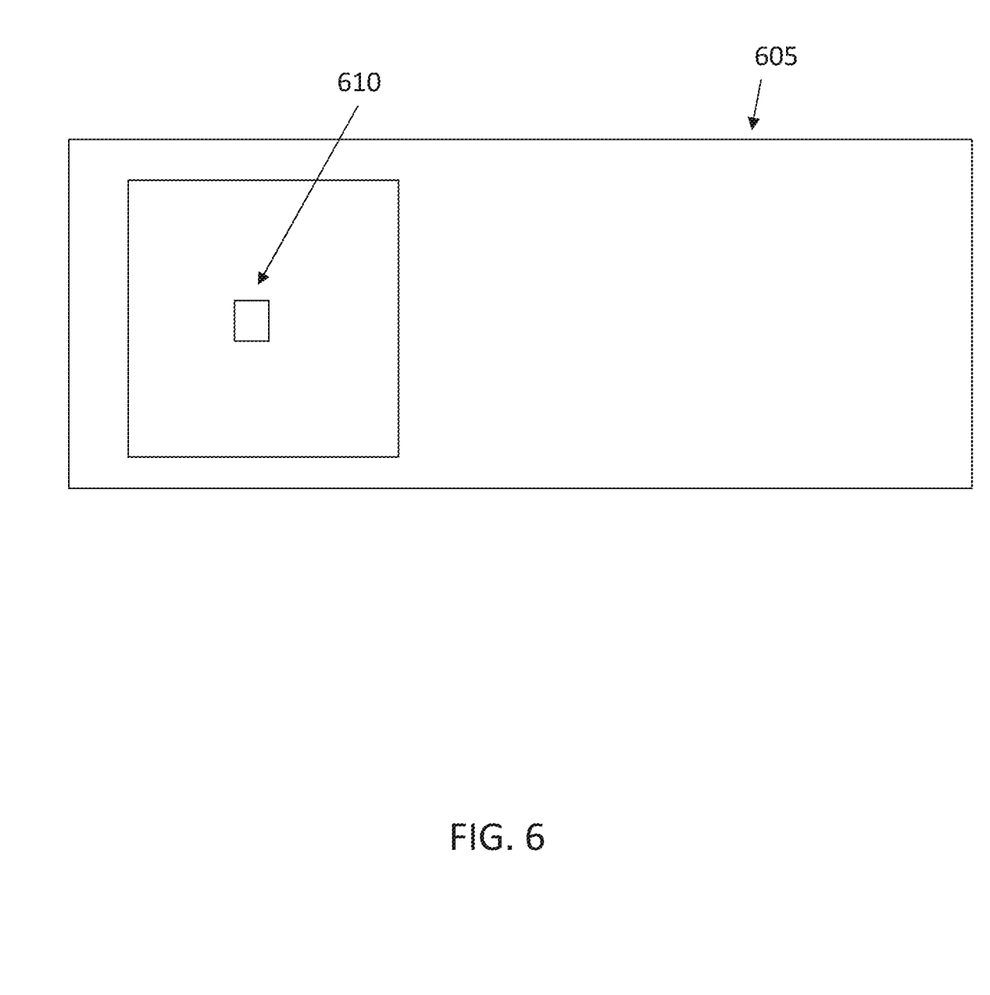

The present disclosure describes a device which employs a CMOS microchip chemical sensor embedded in a bandage. The sensor chip can be either battery powered or remotely powered through inductive coupling of RF frequency power (RF tag), or through an infrared laser or LED. A CMOS chip can measure either conductivity changes on a working electrode of an electrochemical cell or ion current from an enzyme reaction or dielectric constant changes. The measurement circuit is a CMOS silicon circuit that can be manufactured in a standard CMOS fabrication line The present disclosure describes a bandage that can be used as a reservoir to supply an enzyme or other chemistry for a chemical reaction that can accelerate wound healing. A CMOS chip circuit can provide enough voltage to electrochemically generate oxygen or chlorine (depending on the applied electrochemical potential) to change the chemistry in a wound. A CMOS chip can report the measured current, conductivity or dielectric constant out to a reader. For example, FIG. 5 illustrates a reader device (505) comprising an area which can communicate wirelessly (510) to the sensing chip in a smart bandage. FIG. 6 illustrates the reader (605) and the chip reading area (610). An exemplary reader uses a coil to power and receive information from the sensor chip. For example, the reader can have a range of 5 mm, ideal for monitoring wounds with smart bandages.

In some embodiments, multiple CMOS chips in a smart bandage can measure different chemistry in the same bandage. A CMOS chip can measure several molecule concentrations simultaneously by using multiple binding or enzyme chemistries on the same electrochemical electrode or on separate electrochemical electrodes. A CMOS chip in a bandage can determine whether the wound has healed or not. A CMOS chip in a bandage can determine whether the wound is infected (sepsis) by measuring local temperature or chemistries indicating infection. A CMOS chip in a bandage can determine whether there is enough oxygen to facilitate wound healing, and can regulate the oxygen electrochemically. In some embodiments, the CMOS chip comprises a coil to receive power from the wireless reader, and to communicate with the reader.

Figure 7:
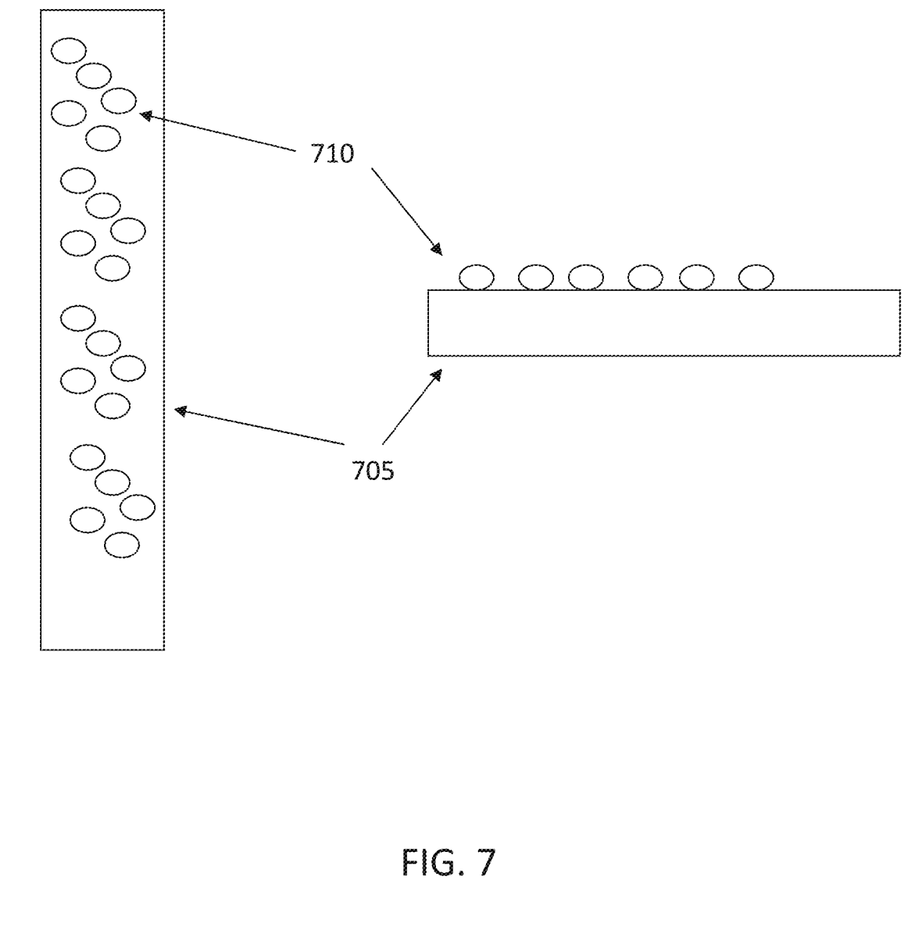
FIG. 7 illustrates an exemplary aptamer functionalization for the electrodes.

FIG. 7 illustrates an exemplary functionalization of electrode surfaces for the chips in a smart bandage. For example, the chip as illustrated in FIG. 1 may have a working electrode, counter electrode and reference electrode in a configuration such as that of FIG. 2, or other, different configurations. The electrodes may, in some embodiments, be made of gold, or have a gold layer as the top surface to be in contact with the wound when the bandage is applied. The electrodes may have a functionalization agent attached to the top surface. For example, if the surface is made of gold, or if the electrode is made of gold, the thiol chemistry may be used to attach biomolecular entities to the electrode surface. One or more of the electrodes may be functionalized in this way. For example, a thrombin binding aptamer with thiols may be attached to the electrode surface. In this way, the electrode can react to the presence and quantity of thrombin and monitor healing of the wound based on the amount of thrombin. For example, the chip can monitor the amount of thrombin as a function of time.

In FIG. 7, the electrode surface (705) is functionalized with a functionalizing agent (710) such as a thrombin binding aptamer. Other aptamers or other functionalizing agents may also be used to detect other molecular targets other than thrombin. In some embodiments, the electrodes may also comprise more than one functionalizing agent in order to detect more than one molecular target.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

What is claimed is:

1. A disposable wound-healing monitoring device comprising:
   a bandage having a first surface configured to face a wound;
   a sensor attached to the bandage on the first surface, the sensor being a complementary metal-oxide semiconductor chip comprising a working electrode, a counter electrode, and a reference electrode; and
   a selectively thrombin-binding or selectively fibrinogen-binding aptarner attached to a wound-facing surface of the working electrode, the counter electrode or the reference electrode,
   wherein the complementary metal-oxide semiconductor chip is configured to monitor an amount of thrombin or fibrinogen in the wound as a function of time by
      detecting over time an absence or presence of thrombin or fibrinogen in the wound based on the selectively thrombin-binding aptamer binding or not binding to thrombin or the selectively fibrinogen-binding aptamer binding or not binding to fibrinogen,
      generating a corresponding signal, and monitoring healing of the wound over time based on said signal.

2. The device of claim 1, wherein the sensor is configured to generate oxygen within the wound.

3. The device of claim 1, wherein the sensor is configured to be powered wirelessly by a reader device, and to communicate wirelessly with the reader device.

4. The device of claim 3, wherein the sensor and the reader device each comprise a coil, the coils configured to transmit power to the sensor and to communicate between the sensor and the reader device.

5. The device of claim 1, further comprising a thiol group attached to the thrombin binding aptamer.

6. The device of claim 1, wherein the working electrode, the counter electrode, and the reference electrode are made in a form of concentric shapes.

7. The device of claim 6, wherein the concentric shapes comprise squares.

8. The device of claim 6, wherein the working electrode, the counter electrode, and the reference electrode are fabricated on a surface of the complementary metal-oxide semiconductor chip.

9. The device of claim 1, further comprising glucose oxidase or glucose dehydrogenase on the working electrode, the device being configured to measure a current on the working electrode, thereby measuring glucose.

10. The device of claim 1, wherein the complementary metal-oxide semiconductor chip is configured to measure a process of hemostasis and inflammation to identify infections in wounds.

\* \* \* \* \*

UNITED STATES PATENT AND TRADEMARK OFFICE
CERTIFICATE OF CORRECTION

Page 1 of 1

PATENT NO. : 11,162,934 B2
APPLICATION NO. : 15/913704
DATED : November 2, 2021
INVENTOR(S) : Axel Scherer It is certified that error appears in the above-identified patent and that said Letters Patent is hereby corrected as shown below:

In the Claims

In Column 6, Lines 54-57 (within Claim 1):
Delete the word "aptarner" and insert -- aptamer --

Signed and Sealed this
Seventh Day of February, 2023

Katherine Kelly Vidal
*Director of the United States Patent and Trademark Office*